US00PP31735P2

(12) United States Plant Patent
Christensen

(10) Patent No.: US PP31,735 P2
(45) Date of Patent: May 5, 2020

(54) ***PEPEROMIA* PLANT NAMED 'MENDOZA'**

(50) Latin Name: *Peperomia caperata*
Varietal Denomination: Mendoza

(71) Applicant: Gartneriet Tingdal Aps, Odense S (DK)

(72) Inventor: Per Siggaard Christensen, Odense S (DK)

(73) Assignee: Gartneriet Tingdal Aps, Odense (DK)

( * ) Notice: Subject to any disclaimer, the term of this patent is extended or adjusted under 35 U.S.C. 154(b) by 0 days.

(21) Appl. No.: 16/501,076

(22) Filed: Feb. 20, 2019

(51) Int. Cl.
*A01H 5/00* (2018.01)

(52) U.S. Cl.
USPC ..... Plt./373

(58) Field of Classification Search
USPC ..... Plt./373
CPC ..... A01H 5/00
See application file for complete search history.

(56) References Cited

PUBLICATIONS

Pluto Plant Variety Database Oct. 2, 2019. p. 1.*

* cited by examiner

*Primary Examiner* — Annette H Para

(57) ABSTRACT

A new cultivar of *Peperomia* plant named 'Mendoza' that is characterized by leaves that are grey with green veins on the upper surface and red on the lower surface, a large number of leaves and a compact habit.

1 Drawing Sheet

Botanical classification: *Peperomia caperata.*
Variety denomination: 'Mendoza'.

BACKGROUND OF THE INVENTION

The present invention relates to a new and distinct cultivar of *Peperomia* plant botanically known as *Peperomia caperata* and hereinafter referred to by the cultivar name 'Mendoza'.

'Mendoza' originated from the crossing of the female or seed parent, *Peperomia caperata* 'Teresa' (not patented) and the male or pollen parent, *Peperomia* 'Eden Rosso' (U.S. Plant Pat. No. 24,379). The crossing was conducted in 2015 in Odense, Denmark. The resulting seeds were subsequently planted and grown. The cultivar 'Mendoza' was selected by the inventor in 2016 in a controlled environment as a single plant within the progeny of the stated cross in a cultivated area of Odense, Denmark.

Asexual reproduction of the new cultivar 'Mendoza' first occurred by leaf cuttings in 2016 in Odense, Denmark. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Mendoza'. These traits in combination distinguish 'Mendoza' as a new and distinct cultivar apart from other existing varieties of *Peperomia* known by the inventor.

1. *Peperomia* 'Mendoza' exhibits leaves that are grey with green veins on the upper surface and red on the lower surface.

2. *Peperomia* 'Mendoza' exhibits a large number of leaves.
3. *Peperomia* 'Mendoza' exhibits a compact habit.

The closest comparison cultivars are *Peperomia* 'Schumi Red' (not patented) and *Peperomia* 'Kirsten' (not patented). 'Mendoza' is distinguishable from 'Schumi Red' by the following characteristics:

1. *Peperomia* 'Mendoza' exhibits leaves that are grey with green veins on the upper surface and red on the lower surface. In comparison, the leaves of 'Schumi Red' are red on both the upper and lower surfaces.
2. *Peperomia* 'Mendoza' exhibits a less compact plant habit than the plant habit of 'Schumi Red'.

'Mendoza' is distinguishable from 'Kirsten' by the following characteristics:

1. *Peperomia* 'Mendoza' exhibits leaves that are grey with green veins on the upper surface and red on the lower surface. In comparison, the leaves of 'Kirsten' are green with silver lines on the upper surface and green on the lower surface.

'Mendoza' is distinguishable from the female parent plant, by the following characteristics:

1. The leaves of 'Mendoza' are grey with green veins on the upper surface and red on the lower surface. In comparison, the leaves of the female parent plant are grey on both the upper and lower surfaces.
2. The leaves of 'Mendoza' are smaller than the leaves of the female parent plant.
3. The petioles of 'Mendoza' are shorter than the petioles of the female parent plant.

'Mendoza' is distinguishable from the male parent plant by the following characteristics:

1. The leaves of 'Mendoza' are grey with green veins on the upper surface and red on the lower surface. In comparison, the leaves of the male parent plant are dark green on the upper surface and red on the lower surface.

2. The leaves of 'Mendoza' do not have ribs or riffles. In comparison, the leaves of the male parent plant have ribs and riffles.

BRIEF DESCRIPTION OF THE DRAWING

The accompanying photograph illustrates the distinguishing traits of *Peperomia* 'Mendoza'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Mendoza'. Data was collected in Odense, Denmark from 30 week old plants grown in a glass greenhouse in 13.0 cm. diameter containers. The time of year was Winter and the temperature range was 20-23 degrees Centigrade during the day and 18-20 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Mendoza' has not been tested under all possible conditions and phenotypic differences may be observed with variations in environmental, climatic, and cultural conditions, however, without any variance in genotype.

Botanical classification: *Peperomia caperata* 'Mendoza'.
Annual or perennial: Perennial.
Parentage: 'Mendoza' is a hybrid of the female parent, *Peperomia* 'Teresa' and the male parent *Peperomia* 'Eden Rosso'.
Plant type: Potted plant.
Growth habit: Rosette of leaves forming very short thick stems.
Plant shape: Flattened globe shaped.
Suitable container size: 7 cm. pots or larger.
Plant height to top of foliage: Average 11.9 cm.
Plant width: Average 26.0 cm.
Vigor: Moderate.
Growth rate: Moderate.
Low temperature tolerance: 10° Centigrade.
High temperature tolerance: 35° Centigrade.
Propagation: Leaf cuttings.
Time to initiate roots (summer): 28 days at 20° C.
Time to initiate roots (winter): 35 days at 20° C.
Time to produce a rooted cutting (summer): 80 days at 20° C.
Time to produce a rooted cutting (winter): 100 days at 20° C.
Crop time: Approximately 30 weeks in Odense, Denmark.
Root system: Fibrous.
Plant fragrance: None.
Stem:
- *Branching habit*.—Very short thick main stems branching into lateral rosettes of leaves.
- *Pinching*.—Not required.
- *Number of main stems per plant*.—Average 8.
- *Number of lateral branches per plant*.—Average 32.
- *Lateral branch dimensions*.—Average 2.5 cm. in length and 0.8 cm. in width.
- *Internode length*.—Less than 0.1 cm.
- *Stem appearance*.—Succulent.
- *Stem shape*.—Rounded.
- *Stem texture*.—Smooth.
- *Stem luster*.—Slightly glossy.
- *Stem pubescence*.—Absent.
- *Stem angle*.—Average 20 degrees.
- *Stem strength*.—Moderately strong.
- *Stem color* (*young*).—146C.
- *Stem color* (*mature*).—Between 148A and 197A.
- *Internode color*.—Between 148A and 197A.

Foliage:
- *Leaf arrangement*.—Alternate.
- *Compound or single*.—Single.
- *Quantity of leaves per lateral branch*.—Average 8.
- *Leaf shape*.—Ovate.
- *Leaf aspect*.—Strongly concave to near cup shaped.
- *Leaf apex*.—Acute to apiculate.
- *Leaf base*.—Hastate, lobes touching to slightly overlapping.
- *Leaf dimensions*.—Average 7.1 cm. in length and 4.1 cm. in width.
- *Texture*.—Glabrous, moderately to strongly leathery (both surfaces).
- *Leaf luster upper surface*.—Glossy.
- *Leaf luster lower surface*.—Moderately glossy.
- *Pubescence*.—Absent (both surfaces).
- *Leaf margin*.—Entire.
- *Leaf lobed*.—Not lobed.
- *Leaf rugose*.—Not rugose (both surfaces).
- *Venation pattern*.—Parallel, strongly furrowed.
- *Young leaf color* (*upper surface*).—198A, veins 200B to 200C.
- *Young leaf color* (*lower surface*).—183C.
- *Mature leaf color* (*upper surface*).—N189C.
- *Mature leaf color* (*lower surface*).—182B.
- *Mature leaf vein color* (*upper surface*).—Between 139A and 147A.
- *Mature leaf vein color* (*lower surface*).—Between 183A and 200B with secondary veins 180A.

Petiole:
- *Petiole dimensions*.—Average 7.1 cm. in length and 0.4 cm. in diameter.
- *Petiole texture*.—Glabrous.
- *Petiole luster*.—Moderately glossy on both sides.
- *Petiole pubescence*.—Absent.
- *Petiole strength*.—Low.
- *Petiole color* (*both sides*).—N148B with fine stripes 181B, stripes more dense toward distal end.

Flower: 'Mendoza' has not produced flowers to date.
Fruit and seed: 'Mendoza' has not produced fruit or seed to date.
Disease and pest resistance: Disease and pest resistance has not been observed.

The invention claimed is:

1. A new and distinct variety of *Peperomia* plant named 'Mendoza' as described and illustrated.

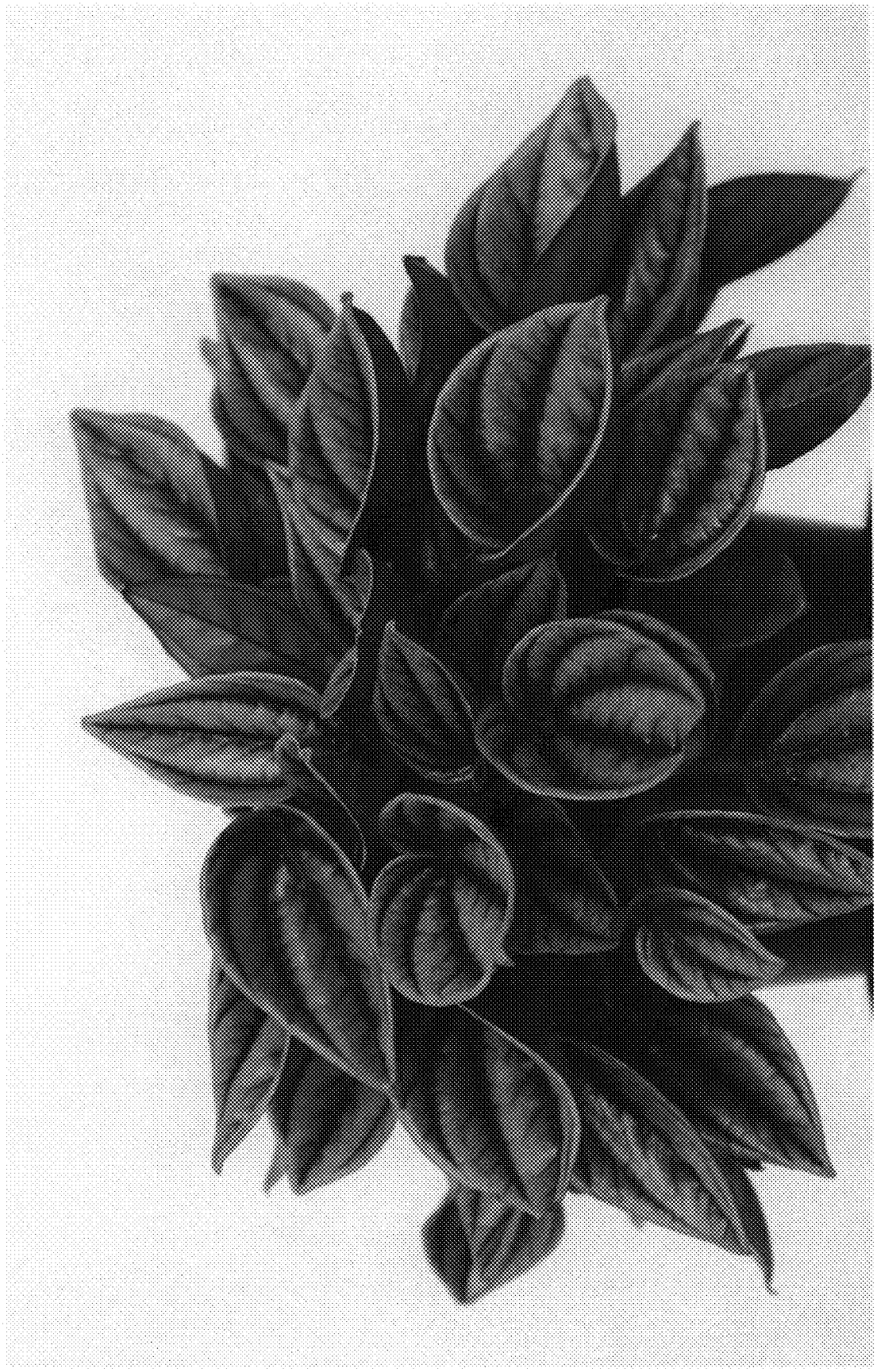

* * * * *